(12) United States Patent
Sederholm et al.

(10) Patent No.: US 7,468,078 B2
(45) Date of Patent: Dec. 23, 2008

(54) MODULAR HIP PROSTHESIS

(75) Inventors: Gary Sederholm, Austin, TX (US); Scott Ely, Austin, TX (US); Kenneth Gustke, Tampa, FL (US); Rodney Plaster, Tulsa, OK (US); Henry Tischler, Great Neck, NY (US)

(73) Assignee: Zimmer, Inc., Waraw, IN (US)

( * ) Notice: Subject to any disclaimer, the term of this patent is extended or adjusted under 35 U.S.C. 154(b) by 0 days.

(21) Appl. No.: 10/613,348

(22) Filed: Jul. 3, 2003

(65) Prior Publication Data

US 2005/0004679 A1  Jan. 6, 2005

(51) Int. Cl.
*A61F 2/36* (2006.01)
*A61F 2/32* (2006.01)

(52) U.S. Cl. .................. 623/22.42; 623/22.46

(58) Field of Classification Search ............... 623/20.34, 623/20.36, 22.41, 22.42, 22.46, 23.15, 23.21, 623/23.22, 23.23, 23.46, 23.47, 22.11, 22.44, 623/22.45
See application file for complete search history.

(56) References Cited

U.S. PATENT DOCUMENTS

| | | | |
|---|---|---|---|
| 5,755,800 A * | 5/1998 | O'Neil et al. ............ | 623/20.16 |
| 5,858,020 A | 1/1999 | Emery et al. | |
| 5,906,644 A * | 5/1999 | Powell ................... | 623/20.15 |
| 6,428,578 B2 * | 8/2002 | White ..................... | 623/23.22 |
| 6,663,670 B2 * | 12/2003 | Rogers et al. ............ | 623/23.47 |
| 6,692,530 B2 * | 2/2004 | Doubler et al. .......... | 623/22.42 |
| 6,875,239 B2 * | 4/2005 | Gerbec et al. ............ | 623/23.15 |
| 2003/0074078 A1 | 4/2003 | Hammill et al. | |
| 2004/0122525 A1 * | 6/2004 | Daniels et al. ........... | 623/22.42 |
| 2005/0004679 A1 * | 1/2005 | Sederholm et al. ....... | 623/22.42 |

FOREIGN PATENT DOCUMENTS

| | | | |
|---|---|---|---|
| DE | 3609120 A1 * | 9/1987 | |
| EP | 634154 A1 * | 1/1995 | |
| WO | WO98/08468 | 3/1998 | |
| WO | WO02/07653 | 1/2002 | |

* cited by examiner

*Primary Examiner*—Dave Willse
*Assistant Examiner*—Javier G Blanco
(74) *Attorney, Agent, or Firm*—Baker & Daniels LLP

(57) ABSTRACT

A modular orthopedic hip prosthesis having three main components: a stem, a proximal body, and a neck. The components are removably connectable and selectively adjustable. The neck is rotationally adjustable about the stem, and the proximal body is both rotationally and axially adjustable about the stem. A collet and locking member hold and lock the proximal body to the stem.

20 Claims, 9 Drawing Sheets

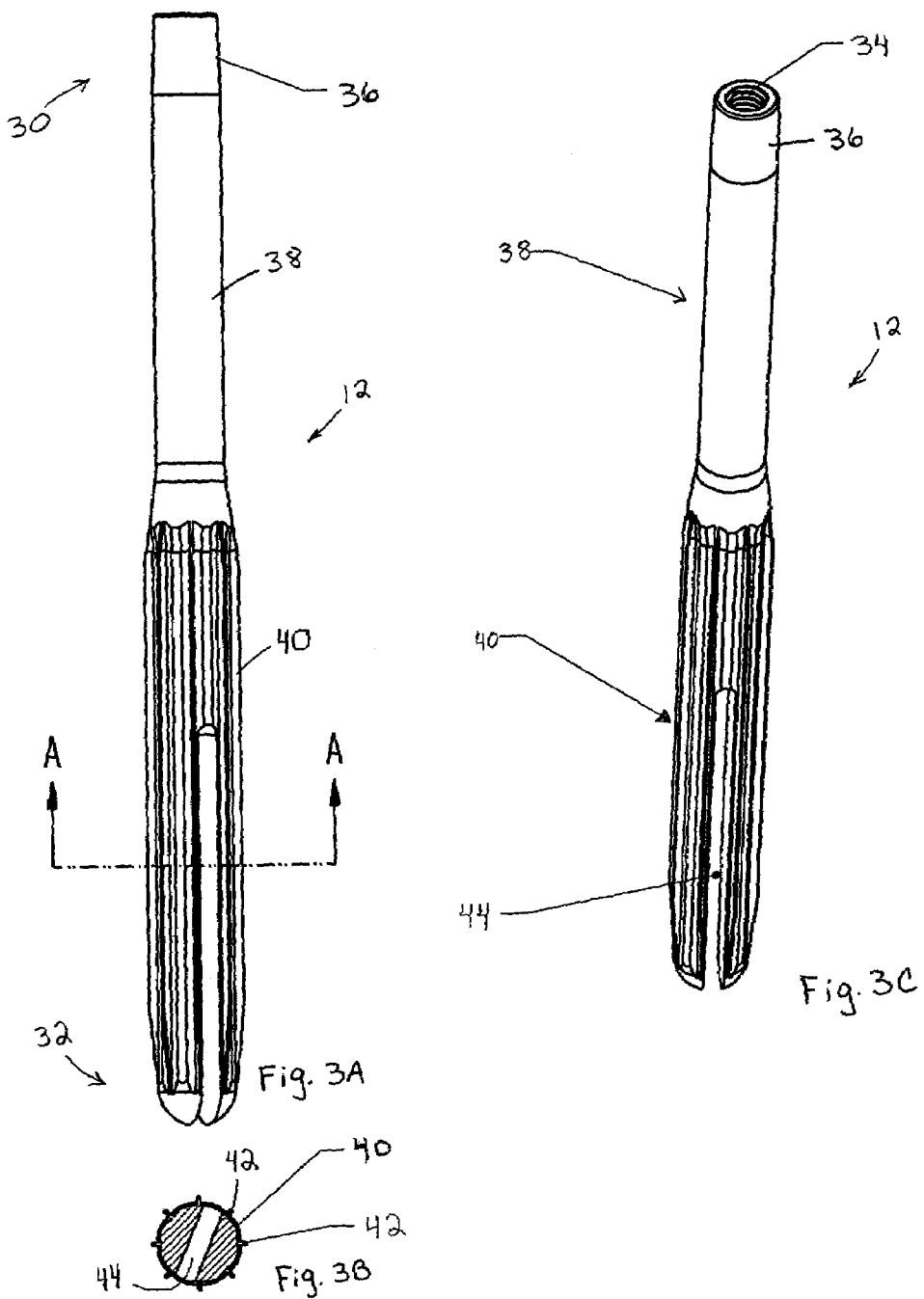

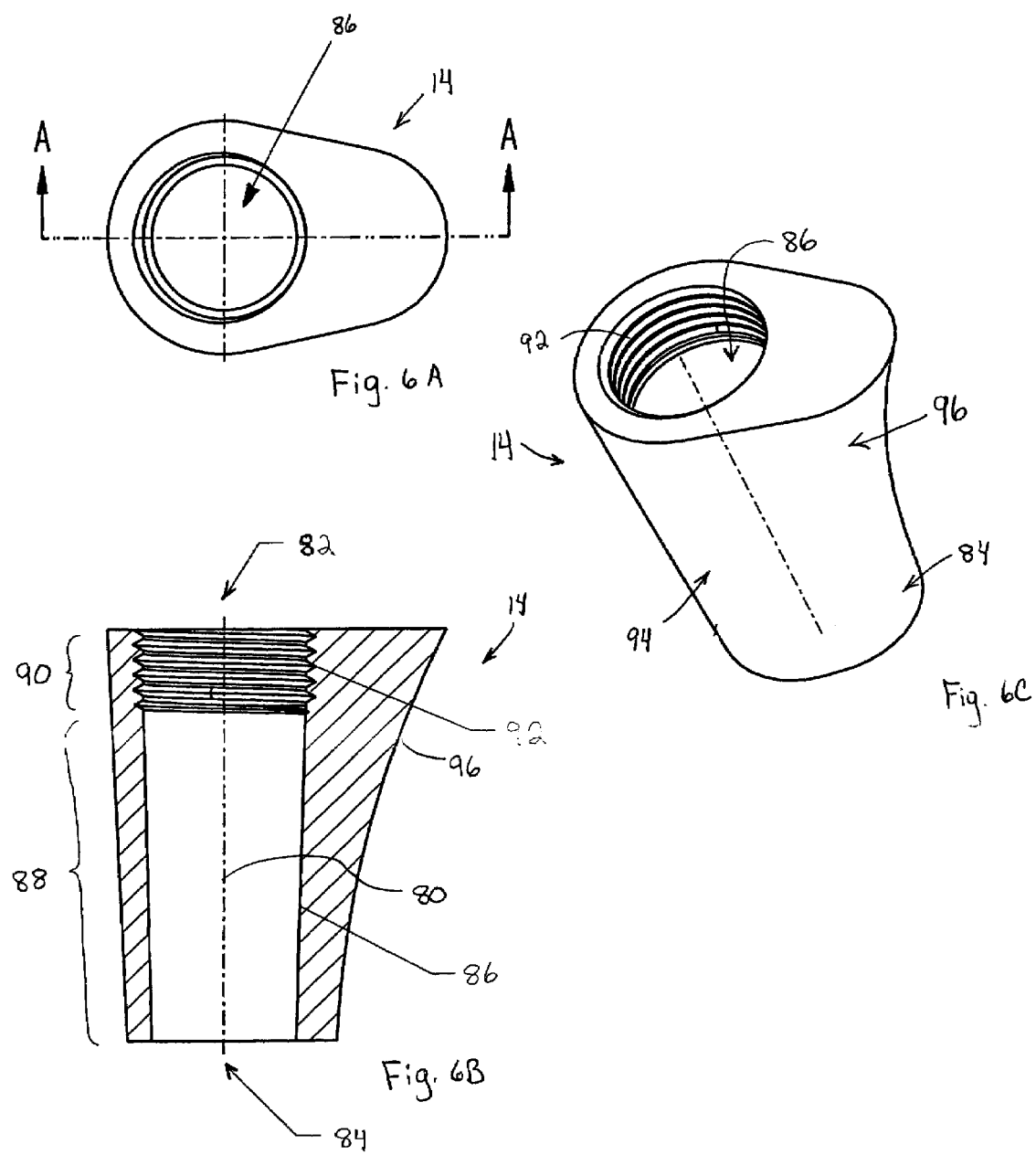

MODULAR HIP PROSTHESIS

FIELD OF THE INVENTION

The disclosure generally relates to implantable orthopedic prostheses for total hip replacement and, more particularly, to a modular hip prosthesis having interchangeable stems, proximal bodies, and necks that are selectively adjustable to conform to various anatomical conditions encountered during a femoral surgical procedure.

BACKGROUND OF THE INVENTION

In hip replacement surgery, the natural head and neck portion of the femur are removed and replaced with a metallic hip prosthesis. This prosthesis generally comprises three elements: a distal stem portion for fixation into the distal part of the femur, a proximal body portion for fixation in the metaphysis of the femur, and a neck portion for replacing the natural femoral neck. These elements can be connected and configured in numerous ways, but generally these elements form either a one-piece prosthetic hip design or a modular prosthetic hip design.

One-piece designs are typically formed from a solid piece of metal, such as titanium, stainless steel, or cobalt chromium alloys. As such, the stem, proximal body, and neck are integrally formed together. Even though the implants are manufactured in a wide range of shapes and sizes, the individual elements cannot be separately altered or sized since no changes or adjustments occur between the elements themselves.

In contrast to one-piece designs, modular designs have some components that are interchangeable. Specifically, modular hip prostheses are formed from individual, separate components that are interchangeable and connectable together. The amount of modularity and degree of adjustability between components varies widely depending on the design and manufacturer of the prosthesis.

Some prior modular designs offer limited modularity between the individual, separate components. U.S. Pat. No. 4,846,839 entitled "Apparatus for Affixing a Prosthesis to Bone" to Noiles teaches, in one embodiment, a proximal body that connects to a stem and neck integrally formed together. Here, the neck has no adjustability since it is permanently affixed to the stem. Further, the proximal body locks to the stem in a single location.

U.S. Pat. No. 5,002,578 entitled "Modular Hip Prosthesis Apparatus and Method" to Lumen teaches, in one embodiment, a femoral neck that connects to a stem and proximal body integrally formed together. The neck is rotationally adjustable about an end of the stem, but the stem and proximal body are not adjustable. In another embodiment, the proximal body attaches to the proximal end of the stem. Here, the proximal body and neck are rotationally adjustable but the proximal body is not axially adjustable along the stem.

U.S. Pat. No. 5,702,480 entitled "Modular Hip Joint Prosthesis" to Kropf et al. teaches a modular prosthesis including a stem, a cervical part, a screw, a coupling member, and a metaphysary. The metaphysary abuts against a shoulder on the outer surface of the stem while the coupling member connects the cervical part to the metaphysary. The metaphysary has no axial adjustability along the stem.

U.S. Pat. No. 5,725,592 entitled "Modular Prosthesis Having Neck Component Connected to Stem Component Through Cavity in Body Component" and U.S. Pat. No. 5,902,340 entitled "Method of Assembling a Modular Prosthesis Used for Bone Replacement" to White, Hayes, et al. teach multiple embodiments that use multiple interlocking taper connections to connect a stem, proximal body, and neck. In several embodiments, the proximal body includes two tapered sections that taper lock to both the neck and stem. In another embodiment, the proximal body has an internally tapered bore that taper locks to a tapered section on the outer surface of the stem.

U.S. Pat. Nos. 5,876,459 and 5,906,644 entitled "Adjustable Modular Orthopedic Implant" to Powell teach multiple embodiments directed to a femoral hip stem. In one embodiment, the proximal body is integrally formed to the stem, and the neck is positioned in a bore in the end of the stem to rotate about the stem. In another embodiment, the proximal body affixes to a proximal end of the stem that has a tapered section to receive the proximal body. The neck includes a split collet that fits into a bore in the proximal body. In yet another embodiment, the proximal end of the stem has an integrally formed split collet. The proximal body fits over the collet while the neck has an elongated threaded section that threads into a bore that extends into the end of the stem.

U.S. Pat. No. 6,139,584 entitled "Proximal Femoral Sleeve for a Revision Hip Prosthesis" to Ochoa et al. teaches a proximal body with a tapered bore for taper locking with a tapered section of the stem. The proximal body has an eccentric outer surface portion with a symmetrical region and a compensating region for offsetting bone loss or other anatomical anomalies. This proximal body is not axially adjustable along the stem.

U.S. Pat. No. 6,299,648 entitled "Locking Hip Prosthesis" to Doubler and Hammill teaches a stem with a proximal portion that is telescoped into one end of a bore in the trochanter element. The mating surfaces of the shaped rod and the trochanter bore form a rotationally immovable connection. A neck element is telescoped into the other end of the trochanter bore permitting rotational adjustment. All the elements are locked together with a bolt through the neck and stem.

U.S. Pat. No. 6,319,286 entitled "Modular Hip Prosthesis" to Fernandez et al. teaches a proximal body with a bore having two sections. A first section of the bore receives a proximal end of the stem, and a second section of the bore receives a distal portion of the neck.

Other hip designs offer different modularity between the various components. Some designs, for example, use an integrally formed stem and proximal body that are connectable to a removeable neck. In these designs, the neck is modular only with respect to the stem and proximal body component. Some prior modular designs also offer limited adjustability between the individual, separate components.

Prior hip prostheses, then, do not offer sufficient adjustability and modularity between the stem, proximal body, and neck. This lack of adjustability and modularity limit the ability of the hip prosthesis to match various anatomical conditions encountered during a femoral surgical procedure. Specifically, the neck, proximal body, and stem should offer sufficient variability to meet physiologically different sizes, shapes, and proportions. A hip prosthesis with such variability would offer significant advantages over prior prostheses.

It therefore would be advantageous to provide an implantable orthopedic hip prosthesis that offered a wide range of adjustability and modularity between the stem, proximal body, and neck.

SUMMARY OF THE INVENTION

The present invention is directed to implantable orthopedic prostheses for total hip replacement and, more particularly to a modular hip prosthesis having interchangeable stems, proximal bodies, and necks that are selectively adjustable to conform to various anatomical conditions encountered during a femoral surgical procedure.

The prosthesis of the present invention generally comprises three separate components: a stem, a proximal body, and a neck. These three components are removeably connectable together. Specifically, the stem has an elongated cylindrical body with a proximal end having a threaded bore extending into the body. The neck has a tapered bore adapted to receive and engage the proximal end of the stem. This bore completely extends through the neck and is adapted to receive a screw for locking the neck to the stem. The proximal body extends from a proximal end to a distal end and includes a longitudinal tapered bore extending through the body. This bore includes internal threads adjacent the proximal end. A cylindrical sleeve or collet is provided to connect the proximal body to the stem. The collet fits over the stem and wedges between the proximal body and the stem. A threaded locking member, such as a nut, is provided to engage the internal threads on the proximal body and lock the proximal body to the stem or provide a means of capturing the collet.

One advantage of the present invention is that the stem, proximal body, and neck are all modular. These three components can be provided in a system wherein a plurality of differently sized and/or shaped stems, proximal bodies, and necks are provided. These components can be interchanged and removeably connected to each other to form a modular hip prosthesis. This modularity enables various stems, proximal bodies, and necks to be connected together to meet specific anatomical conditions encountered during a surgical procedure.

Another advantage of the present invention is that the hip prosthesis of the present invention offers a wide degree of adjustability between the stem, proximal body, and neck. This adjustability primarily occurs in three ways.

First, the neck is rotationally adjustable to an infinite number of positions about the stem. As such, the neck can be adjusted to match the natural femoral neck anteversion (forward rotation) that is widely variable from patient to patient. An inaccurate anteversion can cause a decrease in range of motion, neck impingement, excessive component wear, and lead to subluxation or even dislocation.

Second, the proximal body is both rotationally and axially adjustable to an infinite number of positions about the stem. This adjustability enables the proximal body to accurately fit within the intramedullary canal of the femur. The femur is basically shaped like a tube that is oval in cross section and that curves and twists along its length. When the proximal body is implanted at a high axial position in the femur, as in a primary surgery, a first degree of rotation is required. Conversely, when the proximal body is implanted at a low axial position in the femur, as in a revision surgery, a second degree of rotation (different than the first degree) is required. In short, the rotational and axial adjustability of the proximal body enable the surgeon to vary the shape of the hip prosthesis to suit the need of the patient. The combination of both axial and rotational adjustments provides a better fit between the proximal body and surrounding femoral bone. As such, bone may be saved and not cut to fit the shape or position of the proximal body.

Third, the st m is axially and rotationally adjustable once inserted inside the intramedullary canal of the patient. This adjustment occurs independent of the position of the proximal body in order to restore and obtain the proper leg length. For example, if the stem is inserted too far into the femur, then the leg length is shortened. On the other hand, if the stem is not inserted far enough into the femur, then the leg length is lengthened.

As another advantage of the present invention, the stem, proximal body, and neck are easily assembled and adjusted. Further, these three components can be disassembled if desired. Disassembly, for example, may be required if a component is replaced.

As another advantage, the three components rigidly and firmly connect and lock together to form the hip prosthesis. The locking arrangement prevents relative motion between the components. Unintended motion between the components can cause particulate debris, corrosion, and partial or complete lack of joint function.

As another advantage, the modular hip prosthesis offers flexibility to the surgeon to prepare bone and to assemble the prosthesis. Specifically, the components can be adjusted to conserve natural bone, as opposed to cutting bone to fit the size and shape of the implant. Further, the modular prosthesis can be assembled either in the femur or outside of the femur. These different locations offer the surgeon different methods for preparing and assembling the modular hip prosthesis. Further, the interchangeability of the components facilitates easier inter-operative and intra-operative changes since the components can be adjusted instead of being completely exchanged.

BRIEF DESCRIPTION OF THE DRAWINGS

FIG. 3A is a side view of the stem.

FIG. 3B is a cross-sectional view taken along the lines A-A of FIG. 3A.

FIG. 3C is a perspective view of the stem.

FIG. 6A is a top view of the proximal body.

FIG. 6B is a cross-sectional view taken along the lines A-A of FIG. 6A.

FIG. 6C is a perspective view of the proximal body.

DETAILED DESCRIPTION

Figure 1:
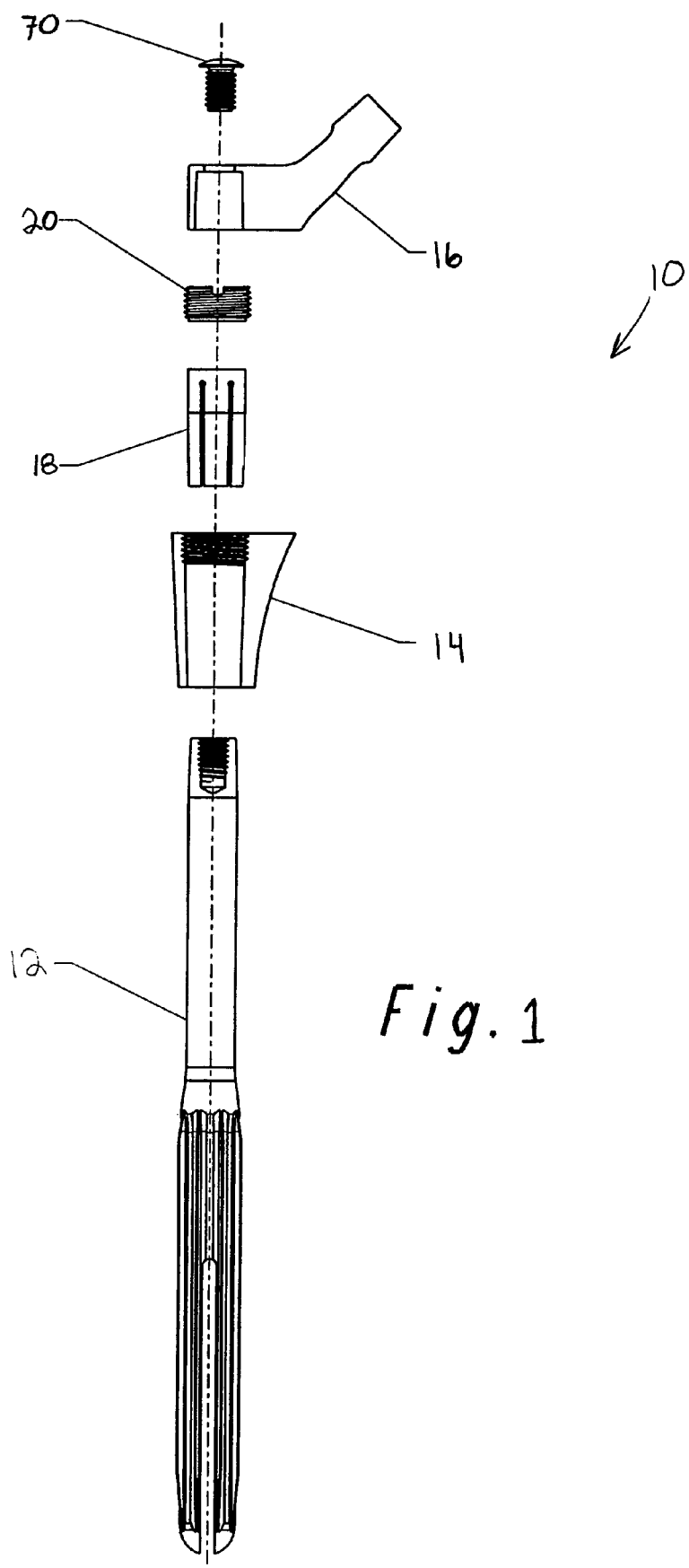
FIG. 1 is an exploded side view showing internal connections of the modular hip prosthesis of the present invention.
Figure 2:
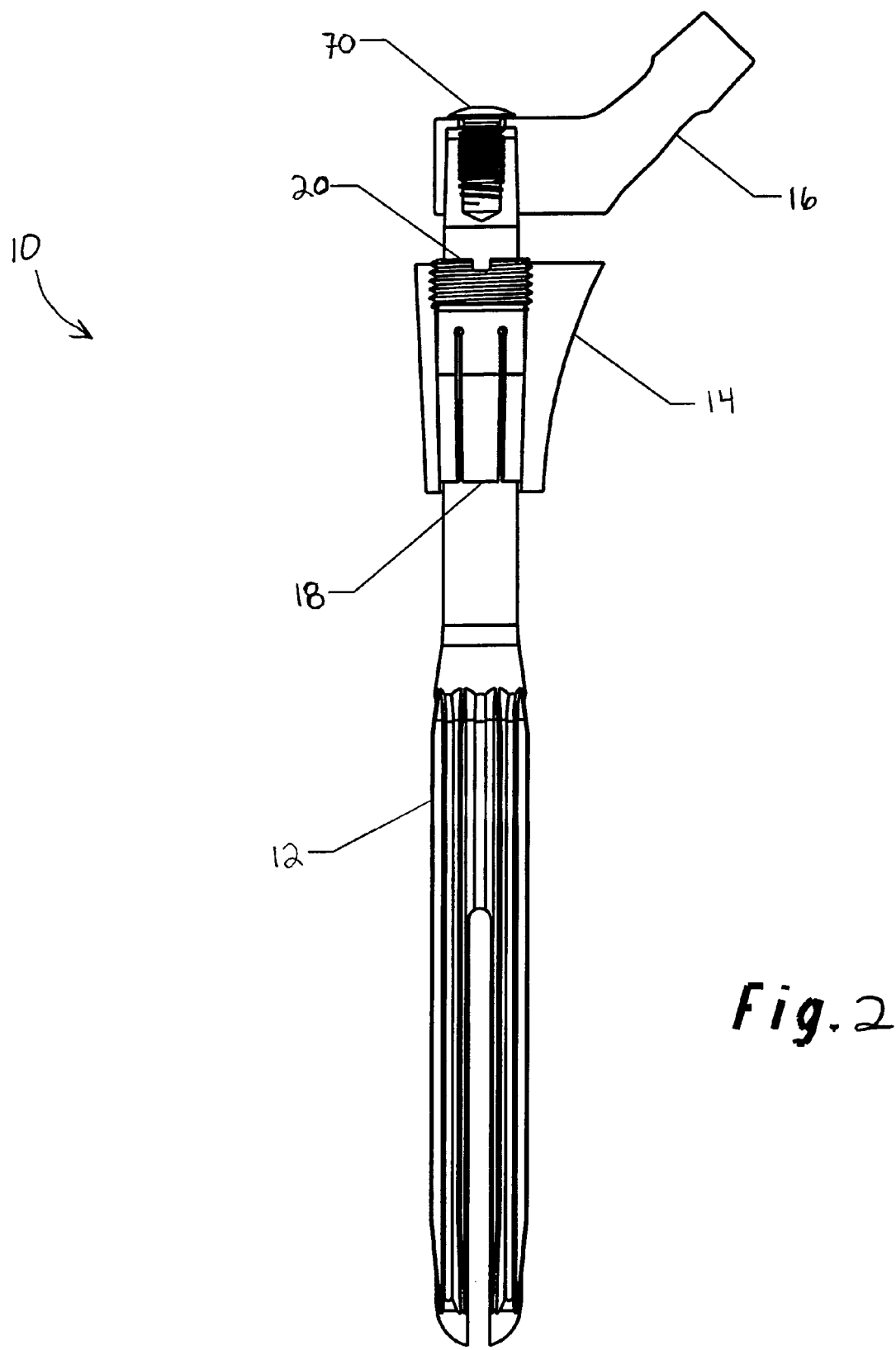
FIG. 2 is a side view showing internal components and connections of an assembled modular hip prosthesis.

FIGS. 1 and 2 show a modular hip prosthesis 10 according to the invention. Prosthesis 10 generally includes three main components: a stem 12, a proximal body 14, and a neck 16.

These components are adjustable with respect to one another and can be assembled and disassembled to form a modular prosthesis. As shown, a collet or sleeve 18 and a locking member 20 form a locking mechanism adapted to affix and lock the proximal body 14 to the stem 12.

Looking also to FIGS. 3A-3C, stem 12 is a separate component and has an elongated generally straight cylindrical body that extends from a proximal region 30 to a distal region 32. The proximal end includes a threaded cylindrical bore 34 that extends into the body. A locking or tapered surface 36 extends along the proximal region. This surface tapers radially inwardly toward the proximal end. An elongated, straight cylindrical section 38 is adjacent the locking surface 36. Section 38 has a smooth external surface and is adapted to receive the proximal body 14. Distal region 32 includes a plurality of flutes 40 that extend along an outer surface of the body of the stem. These flutes 40 are formed between adjacent longitudinal ribs 42 that project outwardly from the body. A slot 44 is formed through the body and extends from a distal end and upwardly toward section 38.

Preferably, the stem 12 is formed as a solid integral component adapted to be positioned and secured into the intramedullary canal of the femur. One skilled in the art will appreciate that the stem could be formed as separate components. The stem, for example, could be formed of two components that are removeably connectable together to form a modular stem. Further, the stem can be provided in a multitude of different lengths, diameters, or even shapes. Preferably, the stem is formed from metal, such as titanium, stainless steel, or cobalt-chromium alloys.

Figure 4A:
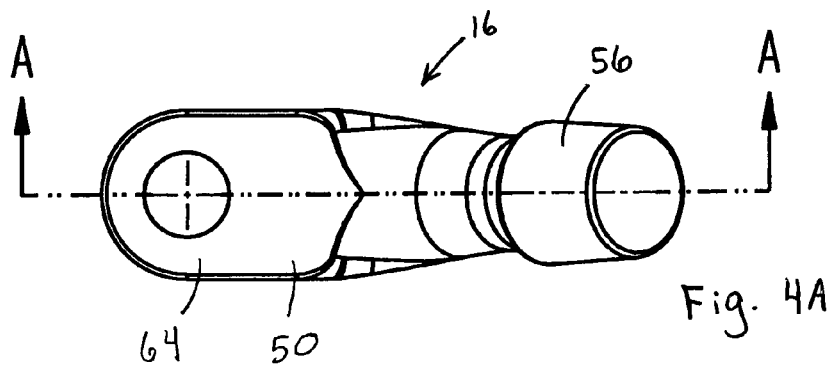
FIG. 4A is a top perspective view of the neck.
Figure 4B:
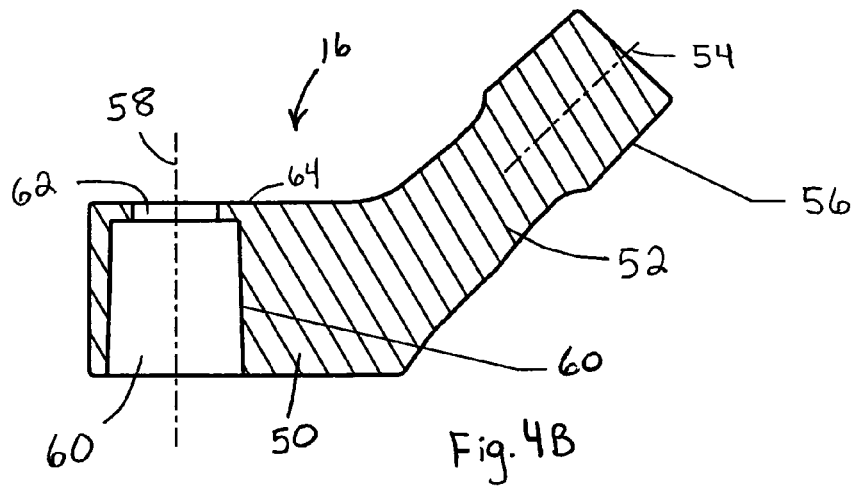
FIG. 4B is a cross-sectional view taken along the lines A-A of FIG. 4A.
Figure 4C:
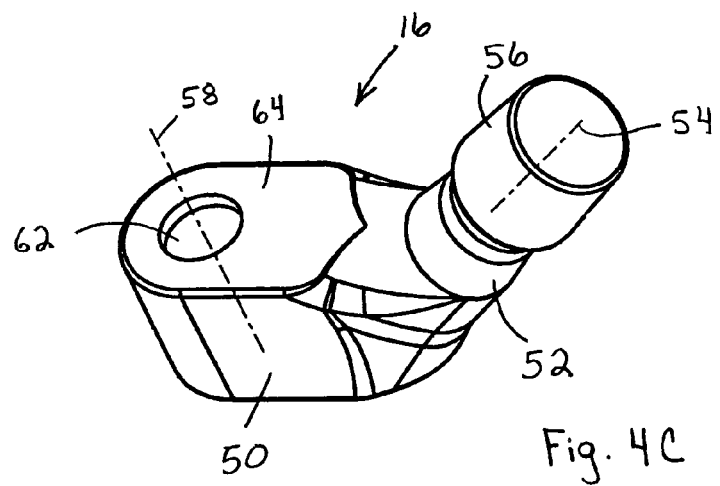
FIG. 4C is a perspective view of the neck.

Looking also to FIGS. 4A-4C, neck 16 is a separate component and includes a generally rectangular base portion 50 and a cylindrical neck portion 52 that extends outwardly from the base portion. The neck portion has a central axis 54 and a joint motion surface that includes a locking or tapered surface 56. Locking surface 56 is adapted to connect to a femoral ball (not shown). Base portion 50 includes a central axis 58 that forms an acute angle with central axis 54. A cylindrical bore 60 is formed in the base portion along central axis 58. This bore has a tapered inner surface and is shaped and sized to engage and taper lock with locking surface 36 of stem 12 (FIGS. 3A and 3C). Base portion 50 also includes a second bore 62 that extends from top surface 64 to communicate with bore 60.

A separate neck that is removeably connectable to the stem is advantageous. In particular, the neck can be offered in a variety of different sizes, shapes, offsets, and heights. This variability increases the possible configurations of the modular hip prosthesis while minimizing inventory.

Figure 5B:
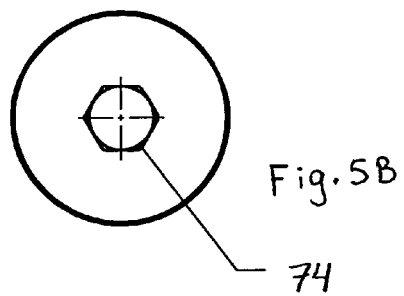
FIG. 5B is a top view of the screw.
Figure 5C:
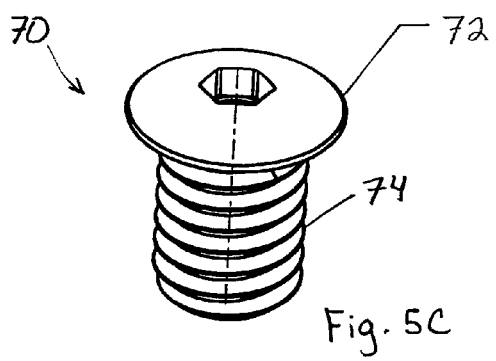
FIG. 5C is a perspective view of the screw.
Figure 5A:
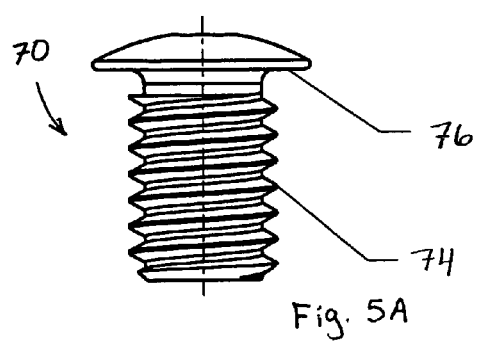
FIG. 5A is a side view of the screw.

FIGS. 5A-5C show a screw 70 having a head portion 72 and a threaded cylindrical shaft 74. Head portion 72 includes a top surface with a tool engaging recess 74 configured as an internal hexagon. A planar locking surface 76 is disposed on the underside of head portion 72.

During assembly, bore 60 of the neck is positioned over the proximal region 30 of the stem so the locking surface 36 engages bore 60. These two components are then pressed together to form a taper lock or connection. Screw 70 is positioned through top surface 64 and into bore 62 until threaded shaft 74 threadably engages threaded bore 34 of stem 12. The screw is tightened so locking surface 76 engages top surface 64.

Looking now to FIGS. 6A-6C, proximal body 14 includes a central axis 80 and extends from a proximal region or end 82 to a distal region or end 84. A cylindrical bore 86 extends completely through the body and forms openings at the proximal and distal ends. This bore forms an internal cavity with two primary sections 88 and 90. Section 88 includes a smooth wall that tapers radially outwardly from the distal end 84 toward the proximal end 82. Section 90 includes internal threads 92.

Proximal body 14 generally has a cylindrical shape at the distal end 84. The body tapers outwardly to form a conical portion 94 and then transitions to a spout 96. Much design and research has been devoted to configuring the size and shape of the proximal body. One skilled in the art will appreciate that the present invention can be employed with proximal bodies having various configurations. These configurations include, but are not limited to, elliptical, tapered, straight, cylindrical, oval, substantially oval, circular, wedge-shaped, key-hole shaped, triangular, conical, frusto-conical, polygonal, and combinations of these configurations.

The proximal body is adapted to fit within the proximal portion of the intramedullary canal of the femur using an interference fit. Preferably, the body is shaped to approximate the internal shape of the femur. Further, the proximal body may be formed from metal, such as titanium, stainless steel, or cobalt-chromium alloys.

Looking now to FIGS. 7A-7D, sleeve 18 is shown in more detail. Sleeve 18 has an elongated cylindrical or tube-like body that extends from a proximal end 100 to a distal end 102. A bore 104 extends completely through the body from the proximal to distal ends. This bore forms a smooth, straight cylindrical wall 106 along the interior. A plurality of longitudinal slots 108 extend upwardly from the distal end toward the proximal end. These slots are parallel to bore 104 and a central axis 110 that extends through the sleeve. These slots, in turn, form a plurality of radially flexible members 112 that have an elongated generally rectangular shape. Members 112 are resilient and adapted to flex radially outwardly or radially compress inwardly.

Figure 7C:
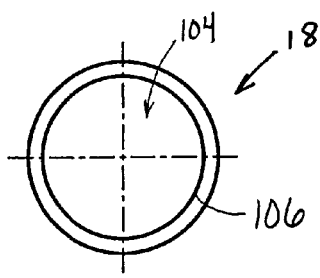
FIG. 7C is a top view of the collet.
Figure 7A:
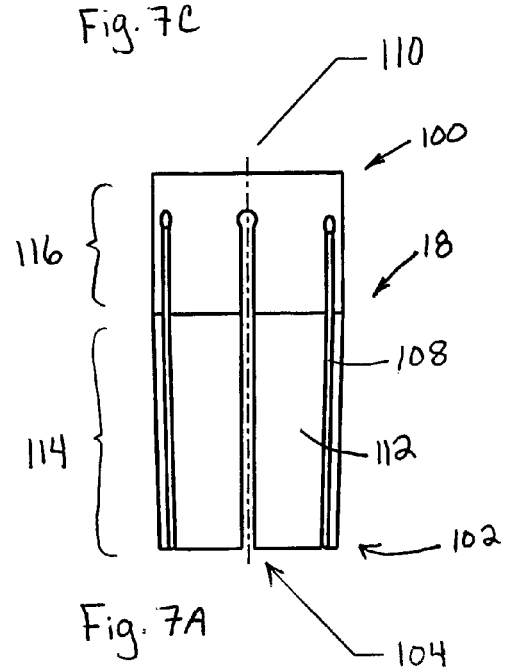
FIG. 7A is a side view of the collet.
Figure 7D:
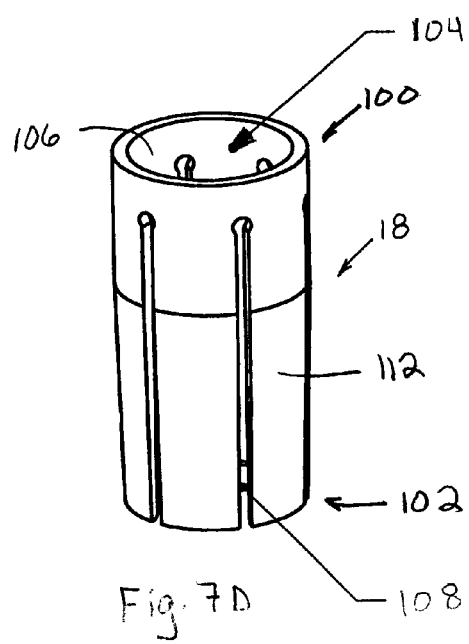
FIG. 7D is a perspective view of the collet.
Figure 7B:
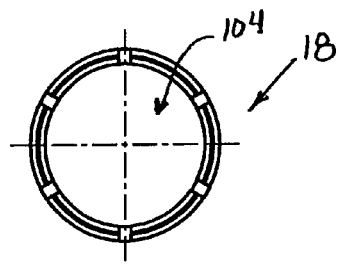
FIG. 7B is a bottom view of the collet.

The external surface of the sleeve has two separate sections 114 and 116 (FIG. 7A). Section 114 is adjacent the distal end 102 and tapers outwardly from the distal end toward the proximal end. Section 116 is adjacent the proximal end 100 and has a straight cylindrical shape.

Preferably, sleeve 18 is configured as a split collet that is formed of a strong durable material. The sleeve, for example, can be formed of metal (such as titanium, stainless steel, or cobalt-chromium alloys) or polymer. Further, sleeve 18 can be formed from a super-elastic material, such as Nitinol.

Figure 8B:
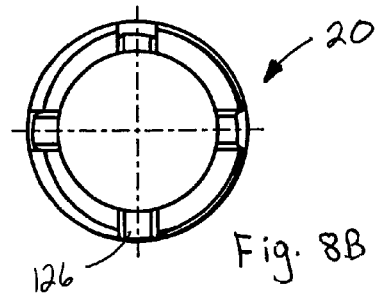
FIG. 8B is a top view of the locking nut.
Figure 8C:
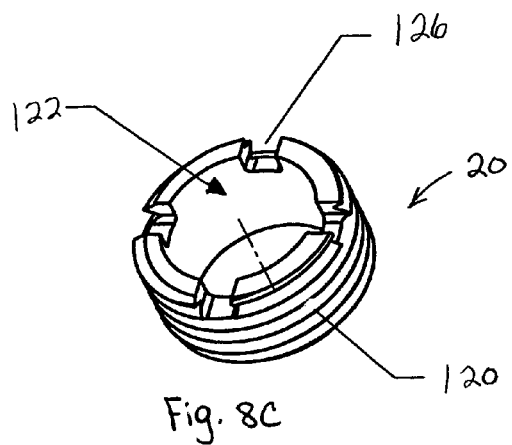
FIG. 8C is a perspective view of the locking nut.
Figure 8A:
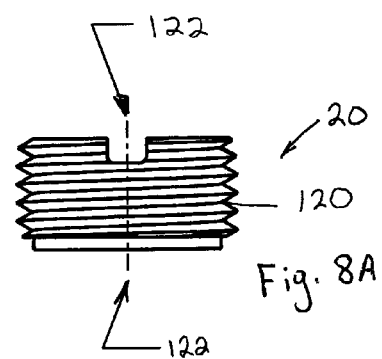
FIG. 8A is a side view of the locking nut.

Turning now to FIGS. 8A-8C, locking member 20 is shown in more detail. This locking member may be formed as a threaded, locking spanner nut. Preferably, the locking member has a cylindrical body shaped like a ring. External threads 120 extend along the outer surface of the body. A cylindrical bore 122 extends completely through the body. This bore is sized and shaped to receive the proximal region 30 of stem 12. A plurality of tool engaging tabs 126 are formed in the body. Four rectangular or square shaped tabs are positioned in a proximal nd of the body and equally spaced circumferentially around the body. These tabs are adapt d to receive a tool for turning or threadably rotating the locking member.

The proximal body 14 can be assembled to the stem 12 in a variety of ways. As one example, the distal end 102 of sleeve 18 can be positioned into the cylindrical bore 86 of proximal body 14 until the sleeve and proximal body engage but do not lock. The sleeve and proximal body are positioned over the proximal region 30 of stem 12 and slideably moveable both axially and rotationally along cylindrical section 38. Once the proximal body is positioned in the desired axial and rotational location on the stem, the sleeve is wedged or forced deeper into bore 86 to radially expand or compress and pressure-lock the proximal body to the stem. At this point, the locking member 20 is threadably engaged with internal threads 92 of section 90 of the proximal body. As locking member 20 tightens, the locking member and proximal body are locked together.

Figure 9:
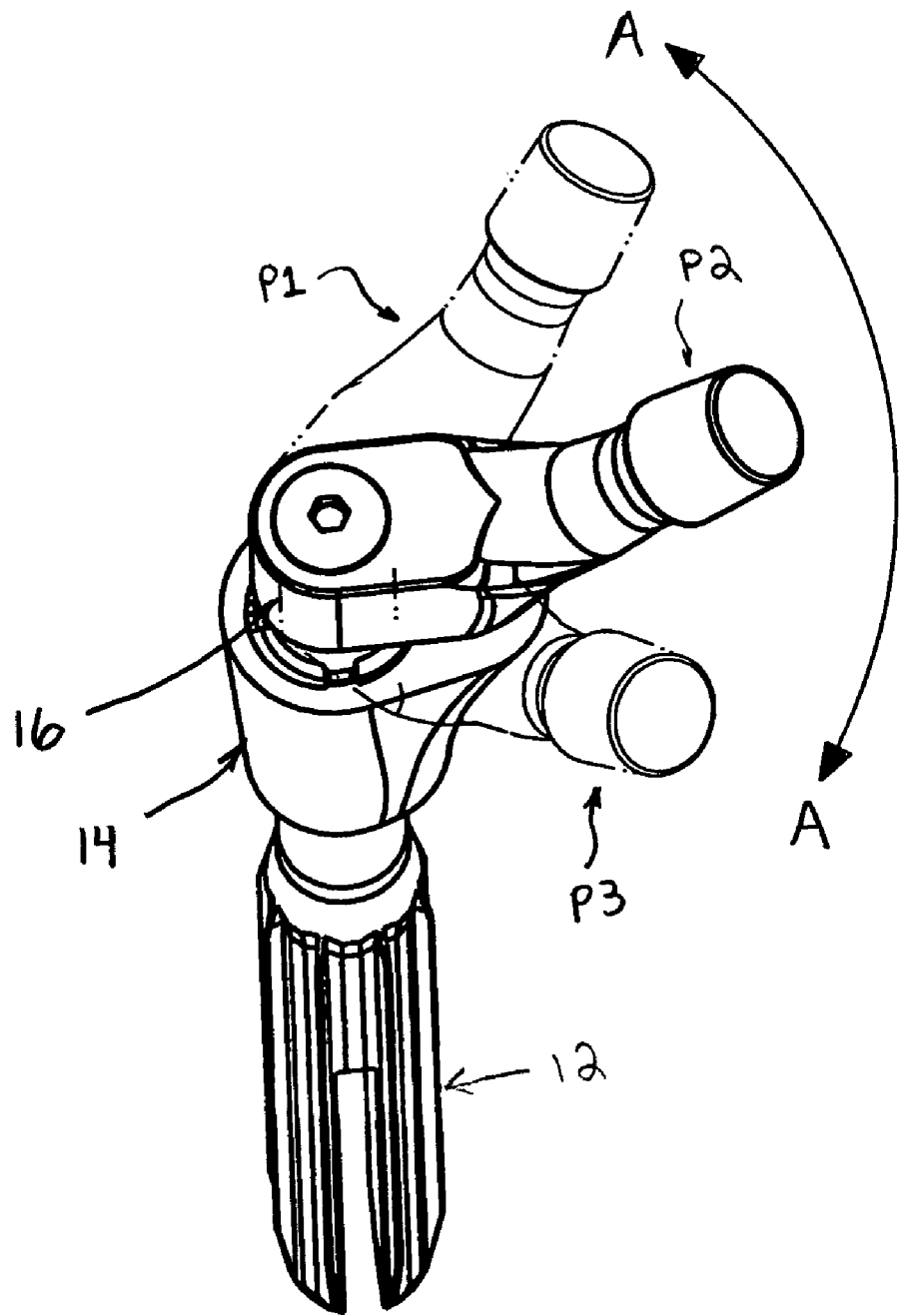
FIG. 9 is a perspective view of an assembled modular hip prosthesis showing rotational adjustment of the neck about the stem.

Looking now to FIG. 9, one advantage of the present invention is that the neck 16 is rotationally adjustable to an infinite number of positions about the stem 12. As shown, neck 16 can be rotationally moved along arrows A-A in either a clockwise or counterclockwise direction. Neck 16 is shown in three different positions: P1 (shown in phantom), P2, and P3 (shown in phantom). The position of the neck is independent of the positions of the proximal body and stem. The neck, thus, can be adjusted to match the natural femoral neck anteversion that is widely variable from patient to patient. Further, the neck anteversion can be independently attained apart from the other components.

Figure 10:
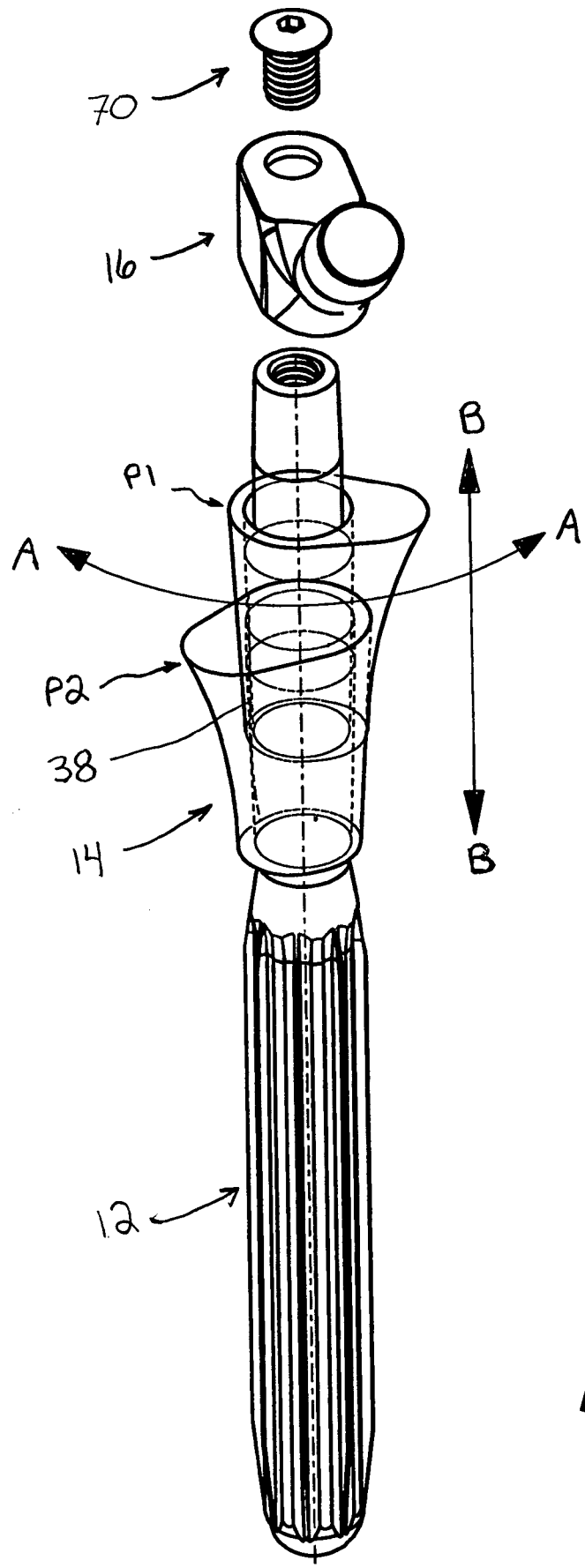
FIG. 10 is a perspective view of a modular hip prosthesis showing both rotational and axial adjustment of the proximal body about the stem.

Looking now to FIG. 10, another advantage of the present invention is that the proximal body 14 is both rotationally and axially adjustable to an infinite number of positions about the stem 12. As shown, proximal body 14 can be rotationally moved on stem 12 along arrows A-A in either a clockwise or counterclockwise direction. Further, proximal body 14 can be axially moved on stem 12 along arrows B-B in either an upward, proximal direction or downward, distal direction. The axial and rotational movement can occur simultaneously and position the proximal body in various positions along section 38. For illustrative purposes, proximal body 14 is shown in two positions: P1 and P2. Preferably, the proximal body is moveable along the stem while the neck 16 and screw 70 are disassembled from the stem. As such, the adjustment of the proximal body occurs independent of the position of the neck. Once the correct axial and rotational positions are obtained, the proximal body is locked to the stem.

Another advantage of the present invention is that the stem, neck, and proximal body can be offered in a variety of different sizes. These differently sized components are separate from each other, interchangeable, and connectable together. A surgeon can choose from a variety of interchangeable stems, necks, and proximal bodies to customize the implant to match the anatomical needs of a particular patient. This modularity between components also reduces the need for large inventories often associated with non-modular hip prostheses.

Although illustrative embodiments have been shown and described, a wide range of modifications, changes, and substitutions is contemplated in the foregoing disclosure; and some features of the embodiments may be employed without a corresponding use of other features. Accordingly, it is appropriate that the appended claims be construed broadly and in a manner consistent with the scope of the embodiments disclosed herein.

What is claimed is:

1. A modular hip prosthesis, comprising:
 an elongated stem extending from a proximal region to a distal region;
 a proximal body having a bore with a threaded section and being removably connectable to the stem;
 a neck connectable to the proximal region of the stem;
 a separate, discrete, expansible collet lockingly positioned between the stem and proximal body, such that the expansible collet is seated radially within the proximal body; and
 a locking member having external threads that threadably engage the threaded section of the proximal body to lock the proximal body and collet together and to the stem, wherein the looking member is seated axially adjacent the expansible collet,
 wherein the neck is movable with respect to the proximal body, until being locked into position by the locking member.

2. The modular hip prosthesis of claim 1 wherein the locking member is a cylindrical nut with external threads.

3. The modular prosthesis of claim 2 wherein the collet forms a taper fit with the proximal body below the threaded section.

4. The modular hip prosthesis of claim 1 wherein the neck is rotationally adjustable about the stem.

5. The modular hip prosthesis of claim 4 wherein the neck is removably connectable to the stem.

6. The modular prosthesis of claim 5 wherein the proximal body is axially adjustable about the stem.

7. The modular prosthesis of claim 6 wherein the proximal body is rotationally adjustable about the stem.

8. A modular hip prosthesis, comprising:
 a femoral stem extending from a proximal region to a distal region;
 a neck being rotationally adjustable about the stem;
 a proximal body being both rotationally and axially adjustable about the stem, the proximal body being positioned around the stem;
 a separate, discrete, expansible collet lockingly engaged between the stem and the proximal body, such that the expansible collet is seated radially within the proximal body; and
 a locking member that engages the proximal body and locks the proximal body to the stem,
 wherein the neck is movable with respect to the proximal body, until being locked into the position by the locking member; and
 further wherein the proximal body includes a threaded section located along an internal longitudinal bore, and the locking member threadably engages the threaded section of the proximal body.

9. The modular hip prosthesis of claim 8 wherein the locking member is positionable over the stem and includes external threads that threadably engage the threaded section of the proximal body.

10. The modular hip prosthesis of claim 9 wherein the locking member has a ring shape.

11. The modular hip prosthesis of claim 8 wherein the proximal body and Neck are removably connectable to the stem.

12. The modular hip prosthesis of claim 8 wherein the neck locks to the proximal region of the stem.

13. The modular hip prosthesis of claim 12 wherein the proximal body locks to the sleeve.

14. The modular hip prosthesis of claim 8 wherein the locking member is an annular member.

15. The modular hip prosthesis of claim 8 wherein the locking member is seated axially adjacent the flexible sleeve.

16. A modular hip prosthesis, comprising:
 a stem extending from a proximal end to a distal end;
 a neck being rotationally adjustable about the stem and removably connected to the proximal end of the stem, said neck including a bore that receives the proximal end of the stem;
 a proximal body being both rotationally and axially adjustable about the stem, the proximal body being positioned around the stem;
 a sleeve separate, discrete, expansible collet lockingly positioned radically between the the stem and the proximal body, wherein the sleeve is radically flexible and includes a purality of longitudinal slots; and a locking member that engages the proximal body to lock the proximal body and sleeve to the stem, wherein the neck is movable with respect to the proximal body, until being locked into position by the locking member; and further wherein the proximal body includes a threaded section located along on internal longitudinal bore, and locking member threadably engages the threaded section of the proximal body.

17. The modular hip prosthesis of claim 16 wherein the proximal body, sleeve, and locking member are separate components.

18. The modular hip prosthesis of claim 17 wherein the proximal body, sleeve, and locking member are removably connectable to the stem.

19. The modular hip prosthesis of claim 16 wherein the locking member is an annular member configured to surround the proximal end of the stem.

20. The modular hip prosthesis of claim 16 wherein the bore in the neck is tapered and is configured to engage a tapered surface on the proximal end of the stem.

* * * * *